US008001235B2

(12) United States Patent
Russ et al.

(10) Patent No.: US 8,001,235 B2
(45) Date of Patent: Aug. 16, 2011

(54) SYSTEM FOR MANAGING PATIENT MEDICAL DATA DERIVED FROM A PLURALITY OF MEDICAL DEVICES

(75) Inventors: Tomas Russ, Carlisle, MA (US); Dina Lynn Latulippe, Methuen, MA (US); Roman Ernesto Pichardo, Medford, MA (US); Wolfgang Scholz, Beverly, MA (US)

(73) Assignee: Draeger Medical Systems, Inc., Andover, MA (US)

( * ) Notice: Subject to any disclaimer, the term of this patent is extended or adjusted under 35 U.S.C. 154(b) by 474 days.

(21) Appl. No.: 11/379,749

(22) Filed: Apr. 21, 2006

(65) Prior Publication Data
US 2006/0242293 A1     Oct. 26, 2006

Related U.S. Application Data

(60) Provisional application No. 60/674,260, filed on Apr. 22, 2005.

(51) Int. Cl.
G06F 15/173     (2006.01)
A61B 5/00       (2006.01)
(52) U.S. Cl. ............ 709/224; 600/300; 600/301; 705/2; 705/3; 128/920; 128/923
(58) Field of Classification Search .................. 600/300, 600/301; 128/903–905, 920, 200, 204.23, 128/204.18; 701/213; 340/593.13, 825.49, 340/5.64; 715/744–747, 864–866, 762–765; 709/201–253, 200; 369/30.2, 30.21–30.29, 369/30.3, 292; 707/705–788, 821–831, 899
See application file for complete search history.

(56) References Cited

U.S. PATENT DOCUMENTS

| 5,912,656 | A  | * | 6/1999 | Tham et al. ............... 600/300 |
| 6,198,394 | B1 | * | 3/2001 | Jacobsen et al. .......... 600/301 |
| 6,269,339 | B1 | * | 7/2001 | Silver ........................ 600/300 |
| 6,551,243 | B2 | * | 4/2003 | Bocionek et al. ......... 600/300 |
| 6,589,172 | B2 |   | 7/2003 | Williams et al. |
| 6,697,103 | B1 |   | 2/2004 | Fernandez et al. |
| 6,733,495 | B1 |   | 5/2004 | Bek et al. |

(Continued)

FOREIGN PATENT DOCUMENTS

EP     0542413  A1     5/2003

OTHER PUBLICATIONS

UK Examination Report for corresponding UK Application No. 0720645.1 dated Feb. 5, 2010.

*Primary Examiner* — Sam Yao
*Assistant Examiner* — Marie Archer
(74) *Attorney, Agent, or Firm* — Jack Schwartz and Associates, PLLC

(57) ABSTRACT

A system for managing patient medical data derived from at least first and second medical devices acquiring respective medical data from a patient includes a proximity detector, for use by the first medical device, for detecting proximity of the second medical device. A command processor responds to the detection of proximity, by initiating generation of signals: (a) to associate patient medical data acquired by the second medical device with patient medical data acquired by the first medical device, and (b) to process patient medical data acquired by the second medical device together with medical data acquired by the first medical device to provide a composite representation of patient medical data.

17 Claims, 2 Drawing Sheets

U.S. PATENT DOCUMENTS

| | | |
|---|---|---|
| 6,735,630 B1 | 5/2004 | Gelvin et al. |
| 6,954,148 B2 | 10/2005 | Pulkkinen et al. |
| 2001/0049544 A1 | 12/2001 | Lee |
| 2002/0013518 A1* | 1/2002 | West et al. .................... 600/300 |
| 2003/0146847 A1 | 8/2003 | Swetlik et al. |
| 2004/0088027 A1 | 5/2004 | Burnes et al. |
| 2005/0102167 A1* | 5/2005 | Kapoor ............................ 705/3 |
| 2005/0115561 A1* | 6/2005 | Stahmann et al. ....... 128/200.24 |

* cited by examiner

SYSTEM FOR MANAGING PATIENT MEDICAL DATA DERIVED FROM A PLURALITY OF MEDICAL DEVICES

This application derives priority from U.S. Provisional Patent Application Ser. No. 60/674,260, filed on Apr. 22, 2005.

FIELD OF THE INVENTION

The present invention relates generally to the field of medical devices, and more particularly to the processing of data generated by multiple sensors in a patient environment.

BACKGROUND OF THE INVENTION

Clinicians frequently need to monitor physiological parameters of patients admitted to the hospital. The type of physiological or patient monitor used depends on the severity and urgency (termed acuity) of the medical condition of the patient. Occasionally a patient may be connected to more than one monitor at the same time. For example, a patient may be connected to a limited parameter monitor while the clinician needs to periodically observe a few physiological parameters. In other cases, the patient acuity level may suddenly change, forcing the immediate connection of the patient to a higher complexity monitor monitoring many physiological parameters. Existing systems condition the respective patient monitoring and/or treatment devices to provide their data separately from the data from the other devices. The clinician, thus, monitors separate data views from the different devices. Such systems fail in such cases to manage patient medical data in a manner that facilitates clinician understanding and response to the patient condition. A system according to invention principles addresses this deficiency and related problems.

BRIEF SUMMARY OF THE INVENTION

In accordance with principles of the present invention, a system for managing patient medical data derived from at least first and second medical devices acquiring respective medical data from a patient includes a proximity detector, for use by the first medical device, for detecting proximity of the second medical device. A command processor responds to the detection of proximity by initiating generation of signals: (a) to associate patient medical data acquired by the second medical device with patient medical data acquired by the first medical device, and (b) to process patient medical data acquired by the second medical device together with medical data acquired by the first medical device to provide a composite representation of patient medical data.

DETAILED DESCRIPTION OF THE INVENTION

The term processor as used herein is a device and/or set of machine-readable instructions for performing tasks. A processor comprises one or more of: hardware, firmware, and/or software. A processor acts upon information by receiving information from an input device; by manipulating, analyzing, modifying, converting or transmitting information for use by an executable application and/or procedure or an information device; and/or by routing the information to an output device. A processor may use or comprise the capabilities of a controller or microprocessor, for example. A processor may include a display processor or display generator. A display processor or generator is a known element comprising electronic circuitry or software or a combination of both for generating display images or portions thereof. An executable application as used herein comprises code or machine readable instructions for implementing predetermined functions including those of an operating system, patient medical data management system or other information processing system, for example, in response to user command or input. An executable procedure is a segment of code (machine readable instruction), sub-routine, or other distinct section of code or portion of an executable application for performing one or more particular processes and may include performing operations on received input parameters (or in response to received input parameters) and providing resulting output parameters.

Figure 1:
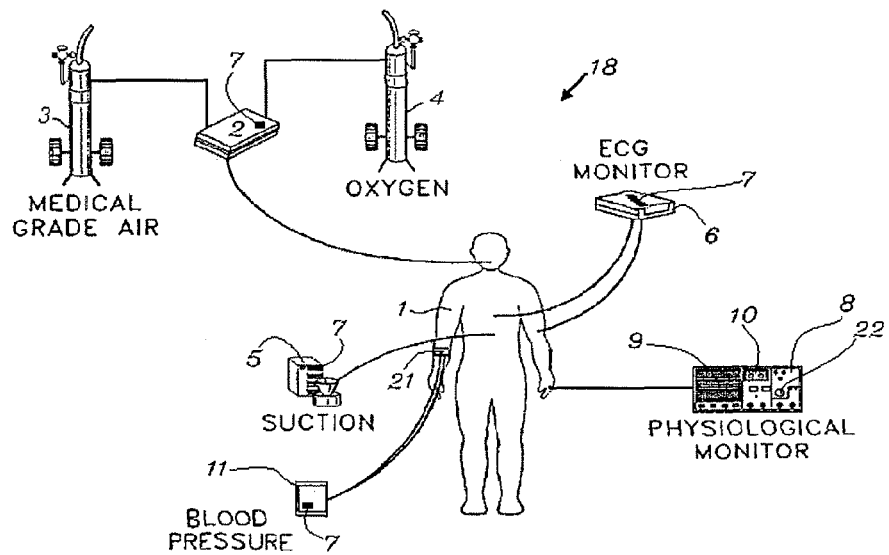
FIG. 1 is a schematic view of a patient interacting with a system according to the principles of the present invention.

Referring to FIG. 1, a system 18 for managing patient medical data according to principles of the present invention may be utilized in conjunction with a patient 1 who is interconnected to a plurality of medical devices, such as medical monitoring and/or treatment devices. The plurality of medical monitoring and/or treatment devices acquire respective medical data from the patient 1. For example, a ventilator 2, capable of supplying either oxygen enriched medical grade air 3 or pure oxygen 4, is attached to the patient 1 and acquires ventilation related medical data. A suction unit 5 is also attached to the patient 1 e.g. to clear an airway or evacuate a wound and provides data representing e.g. the rate and/or volume of material removed. The patient 1 is further attached to an electrocardiogram (ECG) monitor 6 for generating ECG lead signals and a blood pressure measuring device 11.

In FIG. 1, the physiological monitors and treatment devices 2, 5, 6 and 11 are termed low acuity devices, that is, they typically gather patient medical data from the patient 1 but lack a display device, such as a screen. Instead, such devices typically serve as telemetry transmission units, sending the medical data acquired from the patient 1 to another device which receives that data and displays it for use by the clinician. The patient 1 is also attached to a physiological monitor device 8. The physiological monitor device 8 is a multi-parameter monitor having a display screen 9. The physiological monitor device 8 is capable of acquiring patient medical data from the patient and of displaying that data on the display screen 9, and is termed a high acuity device.

At least a first one of the plurality of medical devices includes a radio frequency identification (RFID) tag reader. In a preferred embodiment, a high acuity medical device includes an RFID tag reader. More specifically, in the illustrated embodiment, the physiological monitor device 8 includes an RFID tag reader 10. At least a second one of the plurality of medical devices includes an RFID tag. In the illustrated embodiment, the respective low acuity devices 2, 5, 6, and 11 include RFID tags 7.

Figure 2:
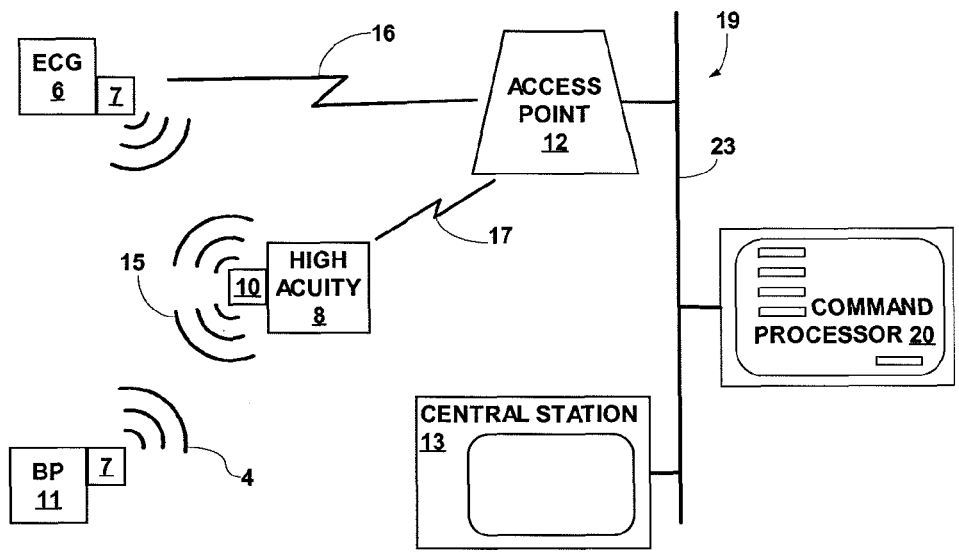
FIG. 2 is a schematic view of the proximity detection and communications functions performed by the system of the present invention as illustrated in FIG. 1.

Referring concurrently to FIG. 2, the high acuity monitor 8 is capable of communicating with the low acuity medical devices 2, 5, 6 and 11 (of FIG. 1). (Only the ECG monitor 6 and the blood pressure monitor 11 are illustrated in FIG. 2 in order to simplify the figure.) The medical devices, 2, 5, 6, 8 and 11 are able to communicate with each other or with other devices through a communications mechanism such as a network 19. The network may include wireless links (e.g. 16, 17) and/or wired links (e.g. 23). The network 19 typically also couples to a command processor 20. The command processor 20 stores data representing at least patient identifier information associated with the patient 1 who is being monitored. Some or all of the functions of the command processor 20 may be performed by an executable application or executable procedure operating in conjunction with a processor. In FIG. 2, the command processor 20 is illustrated as a separate element. However, the command processor 20 may be implemented within the high acuity monitor 8.

In the present example, a patient 1 is initially monitored by the high acuity monitor 8. The medical data acquired by the high acuity monitor 8 is associated with the patient identifier information and an image representing the data is displayed on the display screen 9 of the high acuity monitor 8. The medical data, and associated patient identifier information, may also be transmitted along wireless path 17 to an access point 12, which interconnects the wireless portion of the network 19 (e.g. 16, 17) and the wired portion of the network (e.g. 23). This permits the data to be forwarded via the network 19 from the high acuity monitor 8 to a remote display device having a display processor or generator and a display screen, such as a central station 13. Medical personnel at the central station 13 may concurrently monitor the medical data from more than one patient acquired by medical devices attached to the respective patients.

In the course of providing medical services to the patient 1, a clinician may desire, for example, to measure an additional physiological parameter, such as the patient blood pressure, using the low acuity blood pressure monitoring device 11. The clinician brings the low acuity monitoring device 11 in proximity to the patient 1, attaches the patient 1 to a pressure cuff 21 (FIG. 1), and initiates the blood pressure measurement. Thus, both the first medical device (high acuity monitor 8) and the second medical device (blood pressure monitor 11) are attached to the same patient. Concurrently, the RFID tag reader 10 in the high acuity monitor 8 radiates a radio frequency signal 15 that activates a response signal 4 in RFID tags 7 in nearby low acuity medical devices. At some point during the movement of the blood pressure measuring device 11 toward the patient 1, the RFID tag reader 10 in the high acuity monitor 8 detects the proximity of the RFID tag 7 attached to low acuity blood pressure device 11. That is, in general, the RFID tag reader 10 in a first one of the plurality of medical devices (e.g. the high acuity monitor 8) operates as a proximity detector, for use by the first medical device, for detecting the proximity of a second medical device (e.g. the ECG monitor 6 and/or blood pressure monitor device 11).

The high acuity device 8 communicates with the command processor 20 (e.g. via the network 19) to indicate that a second medical device (e.g. blood pressure monitor device 11) has been detected to be in proximity. In response to the detection of proximity, the command processor 20 initiates generation of signals which associate the patient medical data acquired by the second medical data (blood pressure monitor 11) with the patient medical data acquired by the first medical device (high acuity monitor 8). The network 19, and in particular the wireless portion (16, 17), operates as a communication interface for establishing bidirectional communication between the first and second medical devices to enable acquisition by the first medical device of patient medical data from the second medical device in response to the signals generated by the command processor 20. The network 19 also operates as an interface for establishing communication with a third device (e.g. the central station 13) for communication of patient medical data to the third device. In the illustrated embodiment, the communications link used to establish communication between the first and second medical device, e.g. the network 19, is different than the link used to detect proximity of the second medical device to the first medical device, e.g. RFID tags 7, and RFID tag reader 10.

The signals generated by the command processor 20 also initiate processing of patient medical data acquired by the second medical device (blood pressure monitor 11) together with patient medical data acquired by the first medical device (high acuity monitor 8) to provide a composite representation of the patient medical data. The composite representation of patient medical data may include merged data incorporating the patient medical data acquired by the first and second medical devices. The composite representation of patient medical data may be a signal representing a composite image display incorporating the patient medical data acquired by the first and second medical devices. This composite image display may be displayed on the display screen 9 of the high acuity monitor 8 and/or may be sent to the central station 13 via the network 19 where it is displayed on the display device at the central station 13.

In addition, the blood pressure medical data from the blood pressure monitor 11 is associated with the patient identification information associated with the patient 1. That is, the signals generated by the command processor 20 also associate the medical data acquired by the second medical device (blood pressure monitor 11) with the patient identifier information. The patient identification information may be included in the composite representation of patient medical data and may be displayed on the display screen of the high acuity monitor 8 and/or the central station 13.

In one embodiment, the signal to associate patient medical data acquired by the second medical device with data acquired by the first medical device is generated in response to detection of a user command. This may be desired in some settings in order to enhance safety. More specifically, a confirmation button 22 on the high acuity monitor 8 is present so that the clinician may review and verify the accuracy of the association of patient medical data from respective medical devices with patient identification information. In this embodiment, before the command processor 20 generates the signals which associate patient medical data acquired by the blood pressure monitor 11 with the patient medical data acquired by the high acuity monitor 8 and the identification information of the patient 1, a clinician reviews a display showing details of the proposed association. If it is correct, the clinician activates the confirmation button 22. This conditions the control processor 20 to generate the signals to associate patient medical data acquired by the second medical device with data acquired by the first medical device and with the patient identification information.

In another embodiment, the command processor 20 detects a particular physiological signal. The signal to associate patient medical data acquired by the second medical device with data acquired by the first medical device is generated in response to detection of this physiological signal. More specifically, the command processor 20 detects the blood pressure representative signal from the blood pressure monitor 11. In response to detection of that signal, the command processor 20 generates the signals which associate patient medical data acquired by the blood pressure monitor 11 with the patient medical data acquired by the high acuity monitor 8 and with the identification information of the patient 1. This embodiment may also include user confirmation, as described above.

Figure 3:
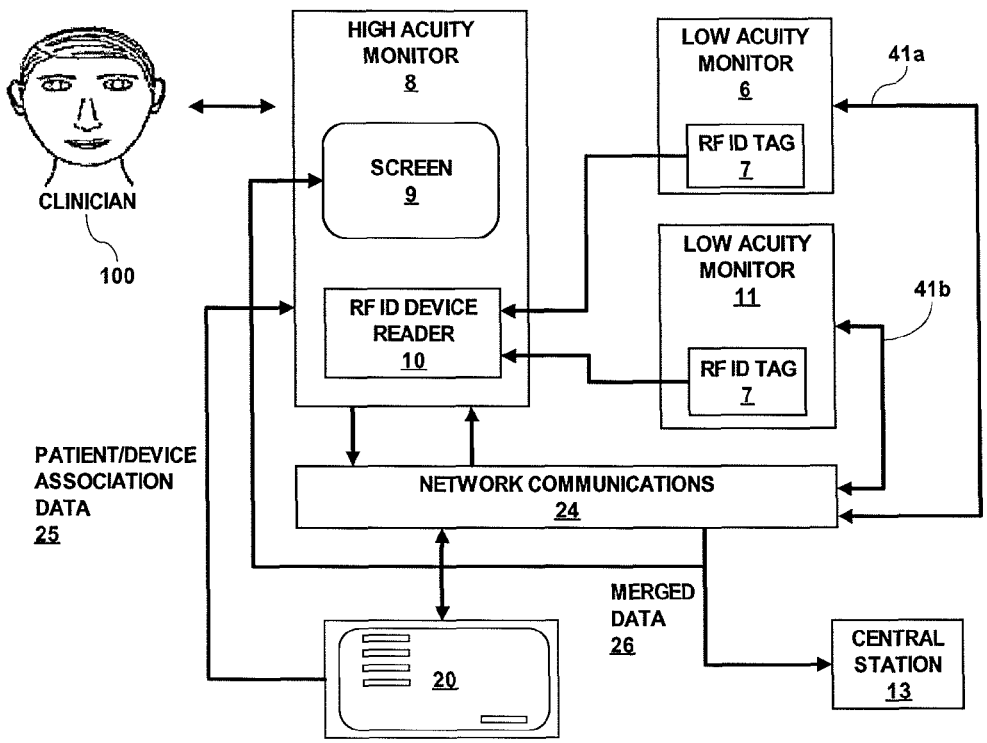
FIG. 3 is a block diagram showing the relationship of the communications network and command processor of the system of the present invention as illustrated in FIG. 1.

Referring to FIG. 3, the operation of the high acuity monitor 8 may be understood. The high acuity monitor 8 provides a clinician 100 with a view of patient medical data, possibly acquired by a plurality of medical devices, via the display screen 9. The high acuity monitor 8 is able to open a network communication interface 24 to at least one low acuity monitor (e.g. ECG monitor 6 and/or blood pressure monitor 11) by using identification information provided by the RFID tag 7. The command processor 20 stores data which associates the identification information contained within the RFID tag 7 with the specific patient 1 and with the respective low acuity devices 6, 11. In particular the associated data includes the physical and/or network address of the low acuity devices 6, 11, that are attached to the patient 1. This patient/device association data 25 is then forwarded to the high acuity monitor 8 by the command processor 20. This allows the high acuity monitor 8 to properly address a network message to the detected low acuity monitors 6,11 via the network communications interface 24.

The high acuity monitor 8 is then able to retrieve, via the network communications interface 24, the ECG data from the low acuity monitor 6 and/or blood pressure medical data from the low acuity monitor 11, for example, and to merge the retrieved data with the patient medical data acquired by the high acuity monitor 8. The high acuity monitor 8 displays this data on the local screen 9. If other patient data is available from the low acuity monitor 6, such as the patient name or gender, the high acuity monitor 8 also retrieves and displays that data. The clinician 100 is then able to view an image representing the merged data 26 acquired from the patient by viewing the high acuity monitor screen 9. The high acuity monitor 8 is also able to transfer the merged data 26 to central station 13 via the network communication interface 24. The central station 13 displays an image representing the merged data instead of separate images representing the respective medical data signals 41a, 41b coming from the low acuity monitors 6, 11.

In an alternate embodiment of the present invention, the high acuity monitor 8 and the low acuity monitors 6 and 11 send respective signals to the central station 13 representing the patient medical data acquired by the separate monitors. Concurrently, the high acuity monitor 8 sends a message to the central station 13 indicating that the separate patient medical data representative signals 41a, 41b supplied to the central station 13 via the network communications interface 24 from the low acuity monitors 6 and 11 are to be merged with the patient medical data representative signal from the high acuity monitor 8 and the merged data associated with the same patient 1 and displayed by the central station 13.

Figure 4:
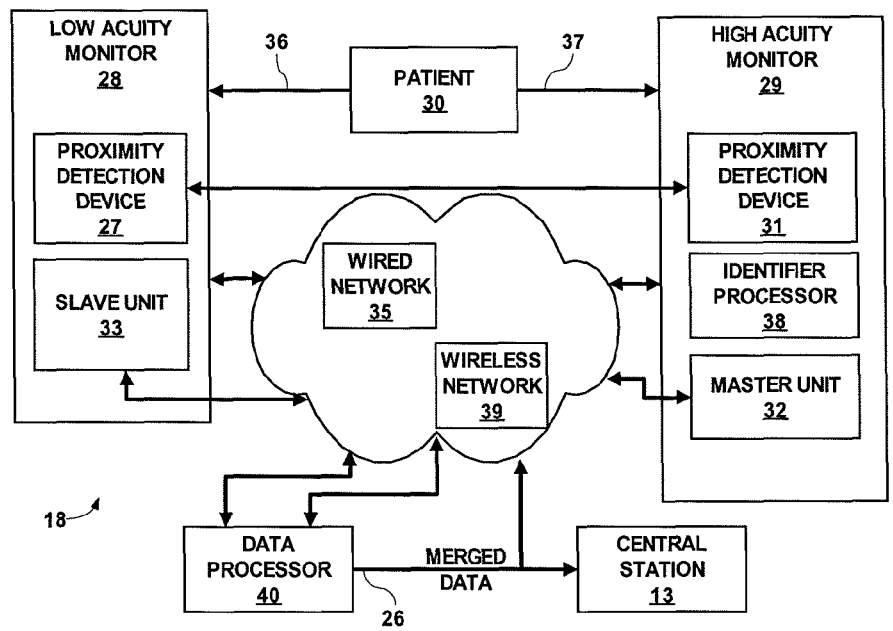
FIG. 4 is a block diagram illustrating an alternate embodiment of a system according to principles of the present invention.

FIG. 4 illustrates additional details of the system 18. For example, alternate proximity detection devices 27 and 31 may be used instead of, or in addition to, RFID devices 7,10 (FIG. 1, FIG. 2). As described above, an RFID tag may be utilized as the proximity detection device 27 in the low acuity monitor 28 and an RFID tag reader as the proximity detection device 31 in the high acuity monitor 29. The high acuity monitor 29 that incorporates an RFID tag reader 31 may be implemented to have a limited range in order to prevent errors in associating multiple devices with a single patient. Other technologies may be used to accomplish the proximity detection function. For example, proximity related communications may be accomplished via a wireless network 39, using a relatively low-power Master/Slave wireless protocol such as Blue Tooth 802.15 standard compatible proximity detection. In that case, the high acuity monitor 29 includes a master unit 32 and the low acuity monitor 28 includes a slave unit 33. Similarly, proximity detection may be accomplished by an infrared data association (IrDA) peer to peer protocol, or by using Global System for Mobile Communications/General Packet Radio Service/Global Positioning System (GSM/GPRS/GPS) standard compatible proximity detection, or any other similar technology in a first medical device which can detect proximity and provide identification information for a second medical device coming within proximity.

The association between the first and second medical devices, e.g. low acuity monitor 28 and high acuity monitor 29, may be effected in several different ways. In one embodiment, the detection of proximity causes association of the two devices 28 and 29 with each other and with the patient 30 to occur automatically. In operation, the high acuity monitor 29 is associated with patient 30 and the proximity detection device, e.g. RFID reader 31, for example, is always operating. The high acuity monitor 29 is thus able to immediately detect and process the presence of the proximity detection device, e.g. RFID tag 27 in the low acuity monitor 28, regardless of the operating status of the low acuity monitor 28. The high acuity monitor 29 contains an identifier processor 38 which is capable of associating patient and device data received from the low acuity monitor 28. Specifically, the identifier processor 38 in the high acuity monitor 29 determines whether the patient identification information and associated patient medical data received from the low acuity monitor 28 corresponds to the patient 30 associated with the high acuity monitor 29, thereby either confirming or rejecting a match between the patient and the received data. If the patient identification information matches, then communication is established between the low acuity monitor 28 and the high acuity monitor 29. A data processor 40, in response to established communications (e.g. the detection of device proximity and a patient match), initiates the generation of signals to associate patient medical data acquired by the medical device 29 with data acquired using the medical device 28 and processes the patient medical data acquired from the medical device 29 together with medical data acquired by the medical device 28 to provide a composite representation of patient medical data.

In an alternate embodiment, association of the devices 28 and 29 with the patient 30 requires detection of proximity and a physiological trigger such as the initiation of a blood pressure measurement or the detection of a plethysmographic signal. In this embodiment the absence of a physiological data signal from the low acuity monitor 28 prevents association of the monitor 28 with the patient 30. In a third embodiment, association occurs when the detection of proximity is confirmed by the clinician 100 (FIG. 3) pressing the confirmation button 22 (FIG. 1) in response to a prompt. In a fourth embodiment, the association may occur only after the reception of a physiological data signal from the low acuity monitor 28 and the confirmation of the association by the clinician 100.

Once the association is established as described above, one of the two monitors, such as low acuity monitor 28, for example, initiates communication with the other monitor (e.g. high acuity monitor 29), via a separate bidirectional communications medium different from the one used to detect proximity and associate the devices. Such a communications medium may be, for example, a connection via a wired network 35 or a wireless network 39 or via a connection including wired and wireless network sections. Using the communications medium, the low acuity monitor 28 is able to merge the patient medical data 36 it acquires with the patient medical data 37 which the high acuity monitor 29 acquires from the patient 30 to create the merged data stream 26. More specifically, in the illustrated embodiment, the data processor 40 receives patient medical data from the low acuity monitor 28 and the high acuity monitor 29 via the network 35, 39, and processes this data to produce merged patient medical data. The merged data 26 is made available to the network 35, 39, and specifically to high acuity monitor 29. This allows the patient medical data from low acuity monitor 28 to be displayed locally on the high acuity monitor 29. Alternatively, the low acuity monitor 28 may send the merged data 26 to other devices in the hospital via the network 35, 39 so that a clinician 100 may view the merged data stream 26 as single set of data even though the data has been acquired by two separate devices 28 and 29. Once the patient/device association is established between the low acuity monitor 28 and the high acuity monitor 29, one of the two monitors may direct a signal to a third device such as the central station 13 to associate the data coming from the two associated devices with the patient 30.

While certain forms of the invention 18 have been illustrated, the invention is not limited to the specific form and arrangement of the parts as described and shown. Various changes may be made by those skilled in this field to the specific embodiments as described without departing from the scope of the invention.

What is claimed is:

1. A system for managing patient medical data derived from a plurality of medical devices acquiring respective medical data and patient identifier information from a patient, comprising:
    a proximity detector, used by a first medical device configured to acquire first patient medical data associated with patient identifier information, that detects proximity of a second medical device, configured to acquire second patient medical data, to the first medical device;
    a command processor that initiates generation of signals upon detecting proximity of the second medical device by said proximity detector to:
    (a) associate the second patient medical data acquired by said second medical device with the first patient medical data acquired by said first medical device and the identifier information of the patient, and
    (b) process the second patient medical data acquired by said second medical device together with the first medical data acquired by said first medical device to provide a composite representation of patient medical data, said composite representation of patient medical data including merged data incorporating said first and second patient medical data acquired using said first medical device and said second medical device;
        a confirmation button selectable by a user that confirms that said composite representation of the patient medical data acquired from respective first and second medical devices are associated with patient identifier information for the same patient; and
    a display processor that initiates display of said merged data.

2. A system according to claim 1 wherein:
    said first medical device acquires the first patient medical data from said patient having a first patient identifier;
    said first and second medical devices are adapted to be attached to the same patient; and
    said signal to associate the second patient medical data acquired by said second medical device with data acquired by said first medical device associates said patient medical data acquired by said second medical device with said first patient identifier.

3. A system according to claim 1 further comprising a network that establishes communication with a third device and communicates said merged data to said third device.

4. A system according to claim 1 wherein said signal to associate the second patient medical data acquired by said second medical device with the first patient medical data acquired by said first medical device is generated in response to at least one of, (a) detection of a particular physiological signal and (b) detection of a user command.

5. A system according to claim 1 further comprising a network that establishes communication between said first and second medical devices to enable acquisition by said first medical device of the second patient medical data from said second medical device in response to a signal generated by said command processor.

6. A system according to claim 5 wherein said network establishes communication between said first and second medical devices by establishing a communication link different than a link used in detecting proximity of said second medical device.

7. A system according to claim 5 wherein said network establishes bidirectional communication between said first and second medical devices.

8. A system according to claim 5 further comprising a data processor that processes patient medical data acquired by said first and second medical devices to provide said composite representation of patient medical data in response to said established communication.

9. A system according to claim 1 wherein said proximity detector comprises a detector using at least one of:
    (a) RFID compatible proximity detection,
    (b) Bluetooth 802.15 standard compatible proximity detection,
    (c) an infra-red proximity detector, and
    (d) GSM/GPRS standard compatible proximity detection.

10. A system for managing patient medical data and patient identifier information derived from a plurality of medical devices, comprising:
    a proximity detector, used by a first medical device configured to acquire first patient medical data associated with patient identifier information from a patient, that detects proximity of a second medical device, configured to acquire second patient medical data from a patient, to the first medical device, said first and second medical devices being adapted to be attached to the same patient;
    a command processor that initiates generation of signals upon detecting proximity of a second medical device by said proximity detector to:
    (a) associate the second patient medical data acquired by said second medical device with the first patient medical data acquired by said first medical device and the identifier information of the patient, and
    (b) process the second patient medical data acquired by said second medical device together with the first patient medical data acquired by said first medical device to provide a composite representation of patient medical data, said composite representation of patient medical data including merged data incorporating said first and second patient medical data acquired using said first medical device and said second medical device;
    a confirmation button selectable by a user that confirms that said composite representation of the patient medical data acquired from respective first and second medical devices are associated with patient identifier information for the same patient; and a network that establishes communication between said first and second medical devices to enable acquisition of said merged data in response to a signal generated by said command processor.

11. A system according to claim 10 wherein the association of second patient medical data acquired by said second medical device with data acquired by said first medical device is generated in response to at least one of, (a) detection of a particular physiological signal and (b) detection of a user command.

12. A system for managing patient medical data and patient identifier information derived from a plurality of medical devices, comprising:
a proximity detector, used by a first medical device configured to acquire first patient medical data associated with patient identifier information from a patient, that detects proximity of a second medical device configured to acquire second patient medical data from a patient, to the first medical device;
an identifier processor that verifies the first and second patient medical data acquired from respective first and second medical devices relates to the same patient by comparing received patient identifier information;
a command processor that initiates generation of signals upon detecting proximity of the second medical device by the proximity detector and verifies the acquired patient medical data from said first and second medical devices relates to the same patient to:
(a) associate the second patient medical data acquired by said second medical device with the first patient medical data acquired by said first medical device, and
(b) process the second patient medical data acquired by said second medical device together with medical data acquired by said first medical device to provide a composite representation of patient medical data, said composite representation of patient medical data including merged data incorporating said patient medical data acquired using said first medical device and said second medical device;
a confirmation button selectable by a user that confirms that said composite representation of the patient medical data acquired from respective first and second medical devices are associated with patient identifier information for the same patient; and
a display processor that initiates display of said merged data.

13. A system according to claim 12 further comprising:
an interface processor that establishes a communication link between said first and second medical devices; and wherein:
said identifier processor receives patient identifier information associated with the second patient medical data acquired by said second medical device in a communication from said second medical device.

14. A system according to claim 12 wherein the association of said second patient medical data acquired by said second medical device with data acquired by said first medical device is generated in response to at least one of, (a) detection of a particular physiological signal and (b) detection of a user command.

15. A method for managing patient medical data derived from a plurality of medical devices, comprising the activities of:
detecting proximity of a second medical device acquiring second patient medical data from a patient to a first medical device acquiring first patient medical data from a patient having a first patient identifier said first and second medical devices being adapted to be attached to the same patient;
confirming that a composite representation of patient medical data including merged data incorporating the patient medical data acquired from respective first and second medical devices are associated with patient identifier information for the same patient;
in response to said detection of proximity and confirmation, initiating generation of signals to:
(a) associate the second patient medical data acquired by said second medical device with the first patient medical data acquired by said first medical device, and
(b) process the second patient medical data acquired by said second medical device together with the first patient medical data acquired by said first medical device to provide said composite representation of patient medical data, said composite representation of patient medical data including merged data incorporating said patient medical data acquired using said first medical device and said second medical device; and
initiating display of said merged data on a display.

16. The method according to claim 15, further comprising the activities of:
establishing a communication link between said first and second medical devices; and
processing respective received patient identifier information associated with the first patient medical data acquired by said first and second medical devices to verify a proper association of received data with a single patient.

17. The method according to claim 15 wherein initiating generation of the signal to associate second patient medical data acquired by said second medical device with patient medical data acquired by said first medical device is performed in response to at least one of, (a) detection of a particular physiological signal and (b) detection of a user command.

* * * * *